United States Patent [19]
Cohen

[11] Patent Number: 4,991,578
[45] Date of Patent: Feb. 12, 1991

[54] METHOD AND SYSTEM FOR IMPLANTING SELF-ANCHORING EPICARDIAL DEFIBRILLATION ELECTRODES

[75] Inventor: Donald M. Cohen, Irvine, Calif.

[73] Assignee: Siemens-Pacesetter, Inc., Sylmar, Calif.

[21] Appl. No.: 333,391

[22] Filed: Apr. 4, 1989

[51] Int. Cl.$^5$ .............................................. A61N 1/39
[52] U.S. Cl. ................................. 128/419 D; 128/785
[58] Field of Search ................... 128/419 D, 785, 784, 128/786, 419 P; 604/21, 53

[56] References Cited

U.S. PATENT DOCUMENTS

| | | | |
|---|---|---|---|
| 3,719,190 | 3/1973 | Avery | 128/418 |
| 3,738,370 | 6/1973 | Charms | 128/419 |
| 3,942,536 | 3/1976 | Mirowski et al. | 128/419 |
| 4,030,509 | 6/1977 | Heilman et al. | 128/419 |
| 4,270,549 | 6/1981 | Mirowski | 128/784 |
| 4,291,707 | 9/1981 | Mirowski | 128/784 |
| 4,355,646 | 10/1982 | Kallok et al. | 128/786 |
| 4,499,907 | 2/1985 | Kallok et al. | 128/786 |
| 4,567,900 | 2/1986 | Moore | 128/784 |
| 4,603,705 | 8/1986 | Mirowski | 128/786 |
| 4,640,298 | 2/1987 | Pless et al. | 128/784 |
| 4,641,656 | 2/1987 | Smits | 128/419 |
| 4,662,377 | 5/1987 | Heilman et al. | 128/419 |
| 4,774,952 | 10/1988 | Smits | 128/419 |
| 4,827,932 | 5/1989 | Ideker et al. | 128/419 |
| 4,865,037 | 9/1989 | Chin et al. | 128/419 D |
| 4,884,567 | 12/1989 | Elliott et al. | 128/419 D |

FOREIGN PATENT DOCUMENTS

0095727 12/1983 European Pat. Off. ............ 128/784

Primary Examiner—William E. Kamm
Assistant Examiner—Scott M. Getzow
Attorney, Agent, or Firm—Bryant R. Gold; Leslie S. Miller; Lisa P. Weinberg

[57] ABSTRACT

A method and system for positioning a defibrillation electrode within the pericardial space of a mammal is disclosed which includes means for distending the pericardium from the heart by injecting a small volume of fluid into the pericardium. A needle having a lumen therethrough is inserted from a sub-xiphoid or other percutaneous position into the body tissue until a tip thereof punctures the distended pericardium at a selected location. A guide wire is inserted into the pericardium through the lumen of the needle, and while the guide wire remains in the pericardial space, the needle is removed. A sheath is introduced over the guide wire, with the aid of a dilator, and inserted into the tissue until one end thereof is positioned within the pericardium. The defibrillation lead, with its electrode in a retracted position, is inserted through the sheath until the electrode is likewise positioned within the pericardium, whereupon the electrode is deployed in order to make contact with a large area of tissue within the pericardium. Additional leads and electrodes may be introduced and deployed in a like manner.

41 Claims, 6 Drawing Sheets

FIG. 11A   MYOCARDIUM        FIG. 11B   MYOCARDIUM

METHOD AND SYSTEM FOR IMPLANTING SELF-ANCHORING EPICARDIAL DEFIBRILLATION ELECTRODES

BACKGROUND OF THE INVENTION

1. Field of the Invention

The present invention relates generally to implantable defibrillation leads and electrodes, and more particularly to methods for the sub-xiphoid implantation of deployable defibrillation electrodes, and means for anchoring the same to tissue within the pericardium.

The pericardium is a membranous sac that encloses the heart. It consists of an outer layer of dense fibrous tissue and an inner serous layer, termed the epicardium, which directly surrounds the heart. Throughout the description and claims that follow, the phrase "within the pericardium" or "within the pericardial space" is used to mean any of the body tissue or fluid found inside of the dense outer layer of the pericardium, including the outer surface of the heart, but not including the interior of the heart.

In recent years a serious effort has been undertaken to implant automatic defibrillators in certain patients at high risk of experiencing ventricular fibrillation or other heart disorders. When fibrillation or related heart malfunctions are sensed by such devices, a large defibrillation shock is automatically delivered to the heart in an attempt to stimulate the heart back to a normal or near normal beating pattern. The advantage of such implanted devices is that the life-saving defibrillation shocks are delivered without any undue delay, as would otherwise exist if external defibrillation pulses had to be delivered by paramedics (or other medical personnel) who were summoned to the aid of a heart-failing patient.

In order to minimize the energy of a defibrillation pulse, and thereby improve the efficacy of the defibrillation system, it is preferred that the defibrillation electrodes be in direct contact with the heart tissue. Further, it is generally preferred that the electrodes cover large and strategic areas of the heart, thereby allowing the delivered electrical energy to be efficiently distributed throughout the fibrillating region. Attempts at placing the defibrillating electrodes on the inside of the heart, either in the atria or the ventricles, or both, similar to stimulating electrodes used with pacemakers, have proven less than satisfactory.

Accordingly, implantable defibrillation electrodes are preferably placed around the exterior of the heart. Because of the large surface area covered by such electrodes, they are typically referred to as "patch electrodes", often resembling patches that are placed on the heart. Although there are some shortcomings associated with placement of defibrillation electrodes directly on the epicardial or endocardial surfaces, the advantages are overwhelming.

In order to make the best possible contact with the heart tissue, it is often desirable that implantable defibrillation electrodes be placed within the pericardium, or within the pericardial space. Unfortunately, however, pericardial placement of defibrillation leads is a dangerous and difficult procedure that has heretofore generally required traumatic and endangering surgery, usually open-chest surgery. Needless to say, not all patients are suitable candidates for open-chest surgery, and even for those that are, the risks, trauma, and danger associated with such surgery make this procedure of electrode placement less than ideal.

In an attempt to minimize the problems associated with open-chest surgery for the placement of epicardial defibrillation leads, it has been suggested in the art to implant epicardial defibrillation leads transvenously. Such an approach is described in patent application Ser. No. 07/128,326, filed Dec. 3, 1987, entitled "Method For Transvenous Implantation of Objects into the Pericardial Space of Patients," jointly invented by the applicant named herein and Clyde D. Elliott. This prior application, including the methods and leads described therein (hereafter referred to as the "transvenous implantation approach"), is hereby incorporated herein by reference.

In accordance with the transvenous implantation approach described in the above-referenced prior application, a guide wire and a catheter are inserted into the heart transvenously, with the aid of an introducer, as required. Once in the heart, the atrial lateral wall is punctured, making a hole therein, through which the non-deployed defibrillation electrode is inserted, thereby entering the pericardial space. The non-deployed electrode is further positioned within the pericardial space to a desired position, and then the electrode is deployed so as to better contact a larger surface area of the outside of the heart.

The transvenous implantation approach also suffers from several drawbacks. For one, a fairly good size hole must be made in the atrial wall, and the trauma and long term effects of such a hole are uncertain. Further, the approach is generally limited to an introducer not much larger than a Fr 14. (A FR 14 instrument is approximately 4.7 millimeters in diameter.) Additionally, the introducer's path is somewhat tortuous, resulting in challenging lead placement. Moreover, once the lead is placed, the ensuing connection of the lead to the site of the implanted defibrillator is non-trivial.

From the venous location of the lead, the lead connector must then be tunneled to the defibrillator site, generally in the abdomen. These limitations place severe restrictions on the geometry and flexibility of the electrode and the deployment system. For small, easily deployed lead systems, the transvenous implantation approach offers a very viable alternative to open chest surgery, particularly if a long tunneled lead is not objectionable. However, in the event very large surface electrodes are desired, or if tunneling is undesirable, the transvenous approach is probably no more effective, and perhaps less effective, than a more direct surgical approach. What is needed, therefore, is a method and system for placing defibrillation leads in the propitious pericardial space that avoids the major problems associated with both the open-chest surgery approach and the transvenous implantation approach. The present invention advantageously addresses this need.

SUMMARY OF THE INVENTION

The disadvantages and limitations of the background art discussed above are overcome by the present invention. With this invention, a method and system for positioning an epicardial defibrillation electrode(s) within the pericardial space are disclosed. Advantageously, the present invention recognizes that a small sub-xiphoid or other percutaneous access into the mediastinum (the space bounded by the two pleural membranes, the pericardium and the diaphragm) can be used to provide a direct access to the pericardium, through which an introducer can be placed.

Such a sub-xiphoid or other introducer can easily be twice the diameter of a subclavian venous introducer, yet its placement can be less painful and cause less damage. Hence, this percutaneous direct access to the pericardial space is preferable over the transvenous implantation approach because it presumably (1) is easier to achieve, and (2) affords more latitude in the lead choice, placement and design, and (3) will entail less mortality and morbidity.

One of the most critical considerations of the method and system of the present invention lies in gaining direct percutaneous access to the pericardial space without puncturing or otherwise damaging the heart. This is because, in the absence of a pericardial effusion, any attempt to introduce a sharp object percutaneously with the intent of piercing the pericardium would almost certainly also invade the myocardium.

To address this concern, the present invention includes means for distending the pericardium from the heart by injecting a small volume of fluid into the pericardium, thus creating a pericardial effusion. This injection extends the pericardium away from the heart. A conventional needle having a lumen therethrough is then inserted from the desired percutaneous location into the body tissue until a tip thereof punctures the distended pericardium at a selected location.

Several means are available for the accurate detection of the moment that the needle tip enters the pericardium before it cuts the epicardium. Among the possibilities are (1) fluoroscopic guidance, (2) monitoring of the force resisting the needle advancement, (3) ECG recording using the needle as an electrode, and (4) pressure monitoring. Perhaps the simplest method may be the most precise and reliable. That is, the egress of the injected fluid through the needle lumen signals that the pericardial space has been entered and that further insertion of the needle can be stopped (else the needle may puncture the heart).

A guide wire is next inserted into the pericardium through the lumen of the needle, whereupon the needle may be removed. A suitable sheath or introducer is then placed over the guide wire and inserted into the tissue until a distal end thereof is positioned within the pericardium. The defibrillation lead, with its electrode in a retracted position, is next inserted through the sheath or introducer until the electrode is likewise positioned within the pericardium, whereupon the electrode is deployed in order to make contact with a large area of tissue within the pericardium.

The preferred percutaneous position from which access to the pericardium is attempted in accordance with the present invention is a sub-xiphoid position. However, it is to be understood that other access paths to the pericardium from a percutaneous location could also be used, such as intercostal access.

The present invention thus includes a method of implanting defibrillation leads within the pericardial space of a mammal that includes the following steps: (a) distending the pericardium; (b) inserting guide means into the distended pericardium from a desired percutaneous position, such as a sub-xiphoid position; (c) inserting the defibrillation lead(s) into the pericardium following these guide means, where following the guide means may include inserting the lead within the guide means or over the guide means, or where the guide means may include two elements and the lead is inserted over one and within the other; and (d) tunneling the body of the defibrillation lead to a desired tissue location, whereat it may be connected to a desired defibrillation device.

Further, the present invention includes a method of positioning defibrillation leads within the pericardium of a mammal. The defibrillation lead(s) used with such a method preferably has a deployable distal electrode means for selectively placing an electrode in contact with a large tissue area when the electrode is deployed, and for selectively maintaining the electrode in a retracted or non-deployed position when the electrode is being inserted through a narrow opening.

This method of positioning includes the steps of: (a) injecting a fluid between the heart and the pericardium, thereby extending the pericardium away from the heart; (b) percutaneously, e.g., sub-xiphoidally, inserting guide means into the extended pericardium to a desired tissue contact location; (c) inserting the electrode, in its retracted position, within the pericardium by following the guide means; and (d) deploying the electrode within the pericardium, thereby making contact with a large tissue area at the desired tissue contact location within the pericardial space.

Moreover, the present invention includes a method for anchoring a distal electrode of a defibrillation lead within the pericardial space. This anchoring method comprises the steps of: (a) capturing an autologous blood clot on the distal electrode; (b) inserting the distal electrode within the pericardium; and (c) coagulating the blood clot to tissue within the pericardium.

Further, the present invention may be characterized as a system for implanting one or more defibrillation leads in a mammal, such as a human, the mammal having a heart surrounded by a pericardium. The defibrillation lead(s) used in such a system preferably has a deployable distal electrode that selectively assumes a retracted or extended position, the retracted position being adapted to promote the positioning of the distal electrode without having the distal electrode becoming entangled with body tissue, and the extended position being adapted to promote contact with body tissue over a large surface area.

However, it is to be emphasized that the implanting system works equally well with non-deployable electrodes. This implanting system includes: means for injecting a fluid between the heart and the pericardium, thereby extending the pericardium away from the heart; means for percutaneously inserting a guide means into the extended pericardium; sheath means for directing a sheath introducer into the pericardium over the guide means; insertion means for inserting the defibrillation lead, with its deployable distal electrode in its retracted position, into the pericardium through the sheath; and deployment means for extending the distal electrode to its extended position once it is positioned as desired within the pericardium.

The present invention is further characterized as a defibrillation lead system that includes: a sheath; means for percutaneously, e.g., sub-xiphoidally, inserting a distal end of the sheath into the pericardial space surrounding the heart; a defibrillation lead having at least one distal electrode, the defibrillation lead being of a size that allows it to be slidably inserted through the sheath until the distal electrode(s) resides within the pericardial space; and means for anchoring the distal electrode to a desired location within the pericardial space.

As will be evident from the description that follows, it is a feature of the present invention to provide a simple, safe and efficacious method and system of implanting one or more defibrillation electrodes into the propitious pericardial space of a mammalian heart.

It is another feature of the invention to provide such a method of epicardial defibrillation electrode placement that is less traumatic and dangerous than prior methods used for this purpose, such as open-chest surgery or transvenous implantation techniques.

It is yet another feature of the invention to provide a flexible implantation method and system that allows a wide range of different types and sizes of electrodes to be implanted in the pericardial space.

It is still a further feature of the invention to provide a means for anchoring a defibrillation electrode to a desired tissue location within the pericardium. Advantageously, this anchoring means utilizes natural bonding mechanisms or agents, such as coagulated blood, to effectuate the desired adhesion between the lead and the pericardium.

DESCRIPTION OF THE DRAWINGS

These and other advantages of the present invention are best understood with reference to the drawings, in which.

DETAILED DESCRIPTION OF THE PREFERRED EMBODIMENT

The following description is of the best presently contemplated mode of practicing the invention. This description is not to be taken in a limiting sense but is made merely for the purpose of describing the general principles of the preferred embodiment of the invention. The scope of the invention should be ascertained with reference to the appended claims.

At the outset, it is noted that the drawings used herein are not intended to be fully detailed representations of the physiological makeup of a mammalian heart and its surrounding pericardium, or of any other part or tissue location of the mammal. Rather, all of the drawings are presented in a very simplified format in order to emphasize the main features and steps of the invention. Most physiological detail has been omitted for clarity. However, it also must be emphasized that the drawings have been selected and designed to provide sufficient detail to enable one skilled in the cardiac medical implantation arts to readily carry out and practice the present invention.

Figure 1:
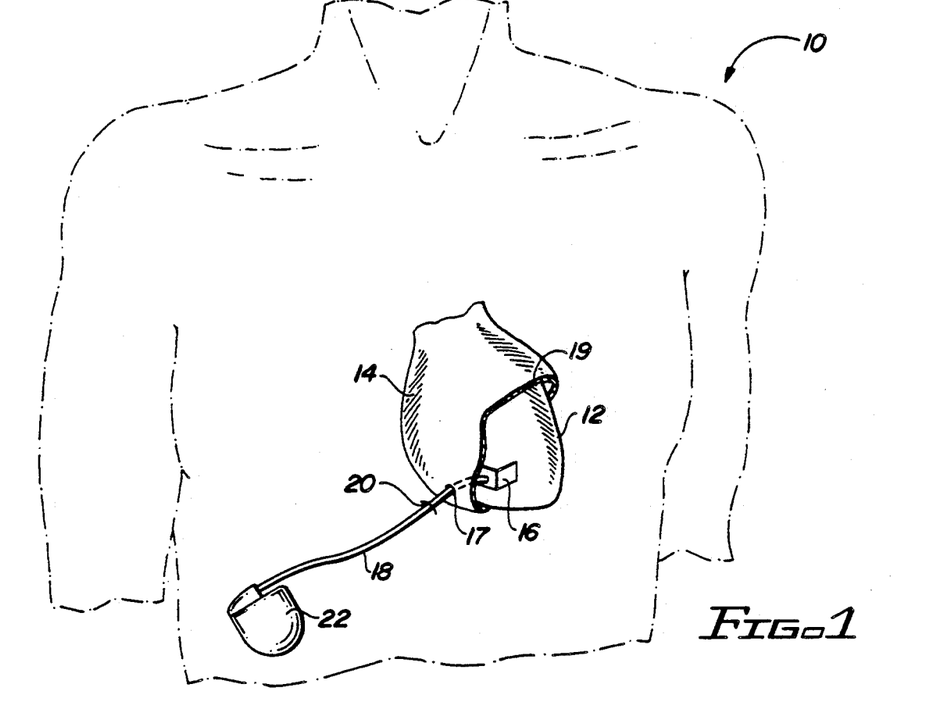
FIG. 1 is a simplified diagram of a mammalian heart surrounded by a pericardium, and further shows a defibrillation electrode positioned therein and connected to an implantable defibrillation device.

Referring then first to FIG. 1, a simplified diagram of a mammalian heart 12 surrounded by a pericardium 14 is illustrated in a simplified format. As an example only, the mammal illustrated in FIG. 1 is a human 10. Further, for clarity, a portion of the pericardium 14 is shown cutaway in order to better illustrate the heart 12 inside of the pericardium. In accordance with the teachings of the present invention, a defibrillation electrode 16, connected to the distal end of a defibrillation lead 18, is passed through an opening 17 within the pericardial wall 19 and positioned within the pericardial space (that space between the exterior heart surface and the interior of the pericardial wall).

Advantageously, this defibrillation lead 18 is directed to the heart from a sub-xiphoid location, i.e., from a location below or underneath the lower end of the xiphoid process below the sternum or breast bone 20. The proximal end of the defibrillation electrode 18 is connected to a suitable defibrillation device 22. The defibrillation device 22 and the lead 18 are preferably implanted within the human 10 using conventional techniques known in the art, i.e., forming a suitable "pocket" within the flesh of the human where the device may be located, and tunneling the lead 18 from the pocket to its sub-xiphoid channel into the pericardial space. As will be apparent from the description that follows, the present invention is directed to a method and system for effectuating and using a sub-xiphoid implantation of a defibrillation electrode, such as is shown in FIG. 1.

In accordance with the method of the present invention, a defibrillation lead is implanted sub-xiphoidally within the pericardial space as follows:

1. The right atrial wall of the heart is perforated with a small opening using a suitable fixation catheter and guide wire, inserted into the heart transvenously. The perforation is limited to the atrial wall and does not traverse the pericardium. This perforation provides access into the pericardial space. Advantageously, this perforation in the atrial wall remains very small (compared to the large perforation required for the transvenous implantation approach described in the previously reference patent application), is used for only a very short period of time, and completely heals over after use.

2. A small volume of fluid (e.g., 25–75 cc for humans), such as saline or renografin, is infused into the pericardial space through the fixation catheter and the opening in the atrial wall. This is done for the purpose of distending the pericardial wall away from the heart in order to facilitate a sub-xiphoid entry into the pericardial space. The volume of fluid infused should be less than the amount that would cause cardiac tamponade and dysfunction.

3. From a sub-xiphoid location, a cardiac needle is inserted into the distended pericardium. Advantageously, the fluid squirts out of the needle lumen to indicate that the needle advancement should be halted before perforating the heart.

4. A guide wire is inserted through the needle into the pericardial space.

5. The needle is removed and a sheath/dilator introducer is inserted into the pericardial space over the guide wire. The opening in the pericardial wall made by the needle is enlarged as required in order to allow the larger introducer to fit therewithin.

6. The distal end of a defibrillation lead is inserted into the pericardium over the guide wire and within the sheath. (Alternatively, at the discretion of the physician, the guide wire may be removed after sheath placement, before lead placement.) This distal end preferably includes a deployable defibrillation electrode having a large area electrode in a retracted position.

7. Once within the pericardial space, the electrode of the defibrillation lead is positioned as desired and the electrode is deployed. Further, the deployed electrode is anchored, as required.

8. Finally, the body of the defibrillation lead is tunneled through body tissue, using conventional methods, to a desired implant location. At this location, a suitable defibrillation device is connected to the lead and implanted, using conventional implant techniques and methods known in the art.

Some of the above steps associated with the method of the present invention are considered conventional in medical implant art, and will not be described further. Other steps require further explanation, as set forth below.

Figure 2A:
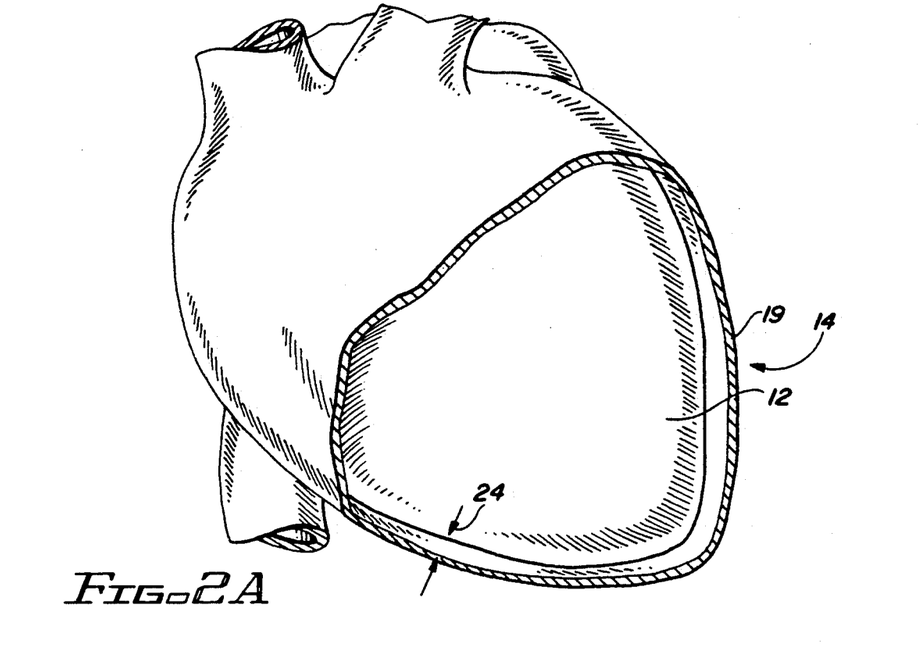
FIG. 2A is a simplified diagram of the heart of FIG. 1 prior to placement of the electrode in the pericardial space.

One of the more difficult aspects of the present invention is gaining sub-xiphoid entry into the pericardial space without puncturing the heart. With reference to FIG. 2A, for example, an expanded simplified view of the heart 12 is shown inside of the pericardium 14, the pericardium being shown in cutaway fashion so as to clearly illustrate the pericardial wall 19 and the space between the pericardial wall and the heart, or the pericardial space 24. This space is shown greatly exaggerated in FIG. 2A for emphasis.

It is not uncommon for the pericardial space 24 to be very narrow in a normal heart, with the inside of the pericardial wall touching, or nearly touching, the exterior of the heart. Hence, it is very difficult to puncture or perforate the pericardial wall 19 without also damaging the myocardium, at the least, or causing tamponade and impending mortality at the worst.

Figures 2B, 3A, 3B, 4:
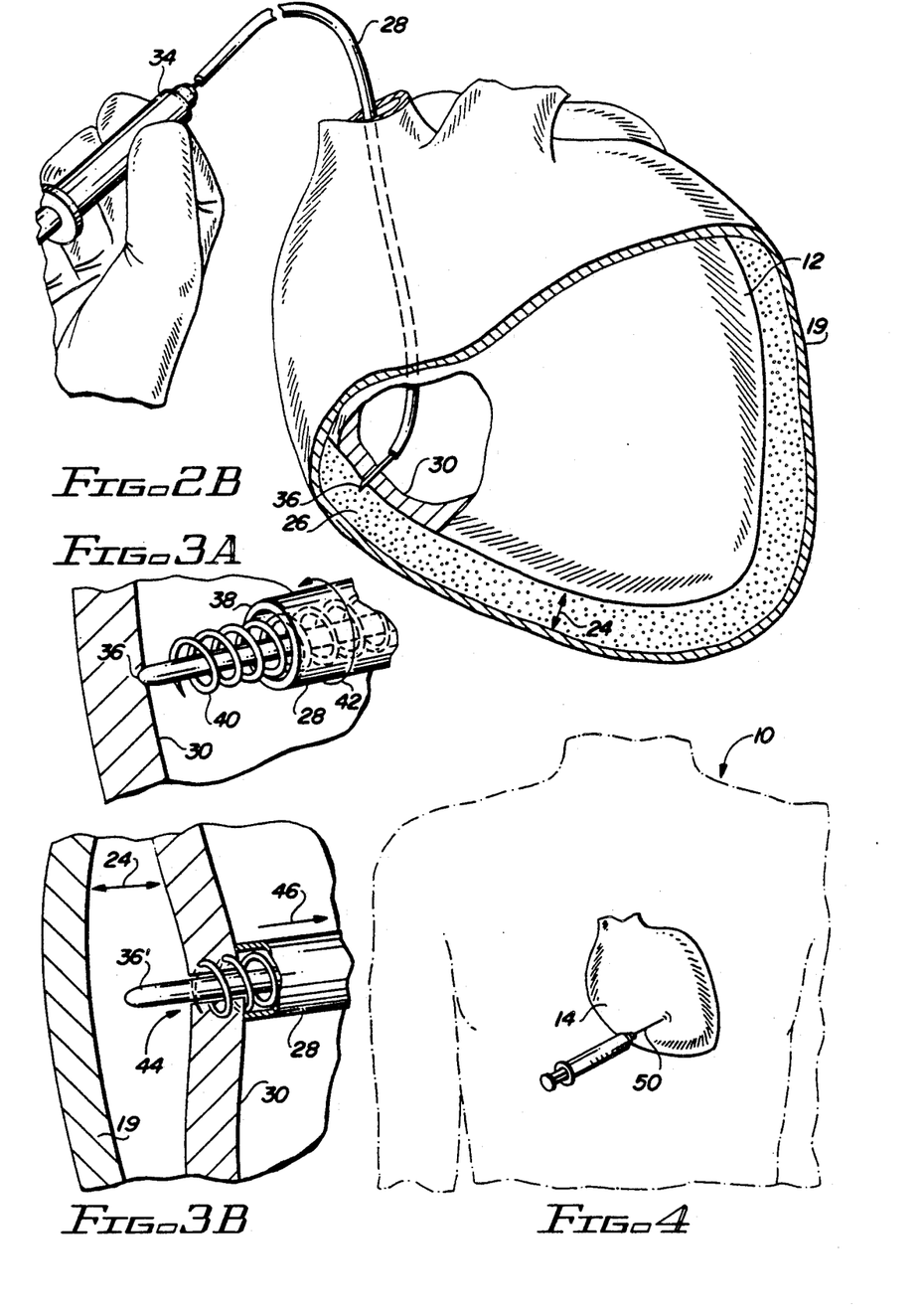
FIG. 2B is a diagram as in FIG. 2A illustrating a distended pericardium resulting from injecting a fluid into the pericardial space through a fixation catheter that has been attached transvenously to the interior of the atrial wall.
FIG. 3A is a schematic perspective view of the fixation catheter of FIG. 2B prior to its attachment to the atrial wall.
FIG. 3B is a schematic perspective view, shown partially in cross section, showing the fixation catheter of FIG. 2B after its attachment to the atrial wall, and further illustrating a J-tip guide wire puncturing the atrial wall to form a hole through which the fluid used to distend the pericardium may be injected.
FIG. 4 is a simplified schematic drawing illustrating the manner of making sub-xiphoid access with a needle to the pericardium.

In order to overcome this difficulty, the present invention contemplates filling the pericardial space with a fluid 26, thereby extending the pericardial wall 19 away from the heart, as shown in FIG. 2B. (In FIG. 2B, the fluid 26 is symbolically represented by small dots placed within the pericardial space 24.) The fluid 26 is injected into the pericardial space 24 through a fixation catheter 28 that is inserted transvenously, e.g., through the jugular or subclavian vein, into the heart and affixed to the interior of the right atrial wall 30.

Once the catheter 28 is secured to the atrial wall 30, a small opening is made in the atrial wall 30 (described below in connection with FIGS. 3A and 3B). This need not be a large opening, and is preferably made with the tip of a suitable stylet or guide wire 36. Once the opening is made, suitable infusion means, such as a hand-held syringe 34, are used to selectively force the desired volume of fluid 26 through the catheter 28 and into the pericardial space 24. The use of a hemostasis valve on the proximal end of the fixation catheter 28 may optionally be used during this process.

It is noted that fixation catheters are known in the art, as is the method of transvenously inserting a catheter or lead into the heart, as guided by a stylet or guide wire placed inside of the catheter or lead. In pacemaker art, for example, it is a very common practice to transvenously insert pacing leads into desired locations, either within the atrium, the ventricle, or both, of a heart using a stylet to guide placement of the distal tip of the lead.

The distal end of the fixation catheter 28 is shown in FIG. 3A prior to fixation thereof to the atrial wall 30. The catheter includes a main body portion 38 made from a tube of silicone rubber (or other body compatible substance) having a helical tip 40 connected to the distal end. The helical tip 40 is designed to be screwed into body tissue by rotation of the catheter. Typically, the helical tip is made from a wire, such as stainless steel wire (or other safe implantable material).

In order to provide adequate torsional stiffness for the catheter 28, yet at the same time to allow suitable flexibility for the catheter, the wire from which the helical tip is made may extend, in a helical wound manner, along the entire length of the catheter 28. During transvenous insertion, the helical tip may be retracted within the tubular wall 38. When the distal end of the catheter tube 38 is positioned at a desired fixation location, as guided by the stylet 36, the helical tip 40 is extended as the entire catheter is rotated, as indicated by the arrow 42, so as to screw the helical tip 40 into the atrial wall 30.

Once the catheter 28 is anchored into the atrial wall 30, a small hole or opening 44 is punched or perforated through the atrial wall using the tip of the stylet wire 36 or equivalent device. One such equivalent puncturing device is shown in FIG. 3, where a J-tip stylet wire 36' is shown inserted through the catheter 28 and through the atrial wall 30.

The preferred puncturing technique is to retract the fixation catheter 28 in the direction shown by the arrow 46 while simultaneously advancing the guide wire 36', so that the atrial wall 30 is separated from the pericardial wall 19, thereby increasing the width of the pericardial space 24 as the guide wire 36' is punctured through the atrial wall 30. This minimizes the likelihood of having the guide wire 36' puncture through both the atrial wall 30 and the pericardial wall 19.

Once the pericardium 14 has been bloated with a fluid, or any other suitable technique is used to distend the pericardium 14 from the heart 12, the next step is to insert a needle 50 into the pericardium from a sub-xiphoid location, as shown in FIG. 4. The goal is to puncture the inflated pericardium with the needle 50, but to avoid having the needle puncture the heart, as is commonly done in the art to relieve cardiac tamponade. This requires a controlled insertion depth of the needle, made easier by simply monitoring the lumen of the needle for egress of the fluid 26 with which the pericardium has been filled.

As illustrated in FIG. 4, application of suction, as with a syringe, while advancing the needle may aid in detecting the presence of the needle tip in the pericardium. Further, some instrumentation can make this sub-xiphoid entry more controlled. It is noted that pericardial drainage is a relatively common and safe procedure for the treatment of patients with pericardial effusions, and the incidence of cardiac perforation is very small.

Further, because of chest movement during respiration, the pericardium may move while pericardial access is being attempted. Hence, it is preferred that a perforation mechanism be used that perforates the pericardium, and then becomes impotent (i.e., unable to further puncture the cardiac wall or any other tissue). Some perforation systems for accomplishing this, besides that described above, are described in connection with the explanation of FIGS. 10A–12D discussed in the Examples presented below.

Figures 5A, 5B:
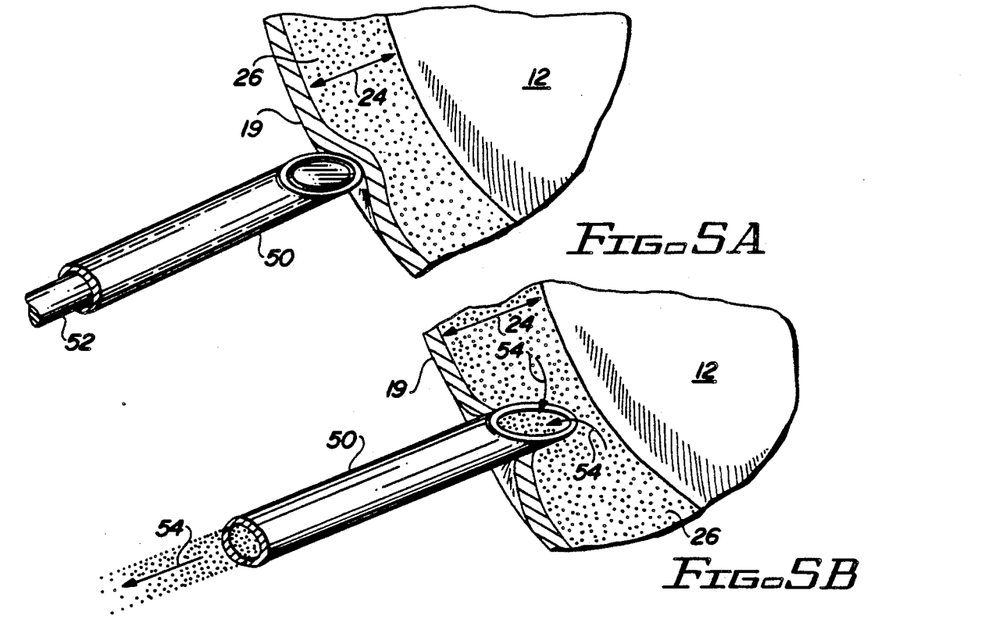
FIG. 5A is an expanded view of the sub-xiphoidally inserted needle tip of FIG. 4 as the needle tip just makes contact with the pericardial wall.
FIG. 5B is a view as in FIG. 5A after the needle tip has punctured the pericardial wall, and further illustrates the fluid in the pericardial space egressing via the lumen in the needle.

Referring next to FIGS. 5A and 5B, the actual perforation of the pericardium 14 will be described. The needle 50 is advanced through the sub-xiphoid tissue into the mediastinum and abutted against the pericardial wall 19, as shown in FIG. 5A. This needle is preferably a blunt metal hypodermic needle tube of a type commonly known in the art. As a tube, the needle has a hole, or lumen, passing longitudinally therethrough. A rod 52 is initially included within the lumen to prevent coring of tissue as the needle is inserted. Neither the needle 50 nor the rod 52 are extremely sharp. At the distal tip, both are slightly angled, but blunt.

At the point where they abut against the pericardium, the pericardium is stretched, but (due to the nature of the pericardial tissue) is not easily perforated. At this point the rod 52 is withdrawn from the needle tube 50 and the needle 50 is further inserted in order to punch through the pericardial wall 19. Once perforation occurs, as illustrated in FIG. 5B, the fluid 26 within the pericardial space 26 begins to egress through the lumen of the needle 50, as illustrated by the arrows 54.

For some patients, as an option to the above method of puncturing the pericardium with a blunt needle, the physician may elect to use a sharper instrument. In accordance with such an option, the rod 52 is withdrawn from the needle lumen and is replaced by a sharp perforation device 56, as illustrated in the exploded view of FIG. 5C. This device 52 fits within the clearance of the needle lumen, and includes a sharp cutting tip 58, a fairly rigid (although somewhat flexible) body portion 60, and a very flexible, compressible coupling portion 62.

Figures 5C, 5D:
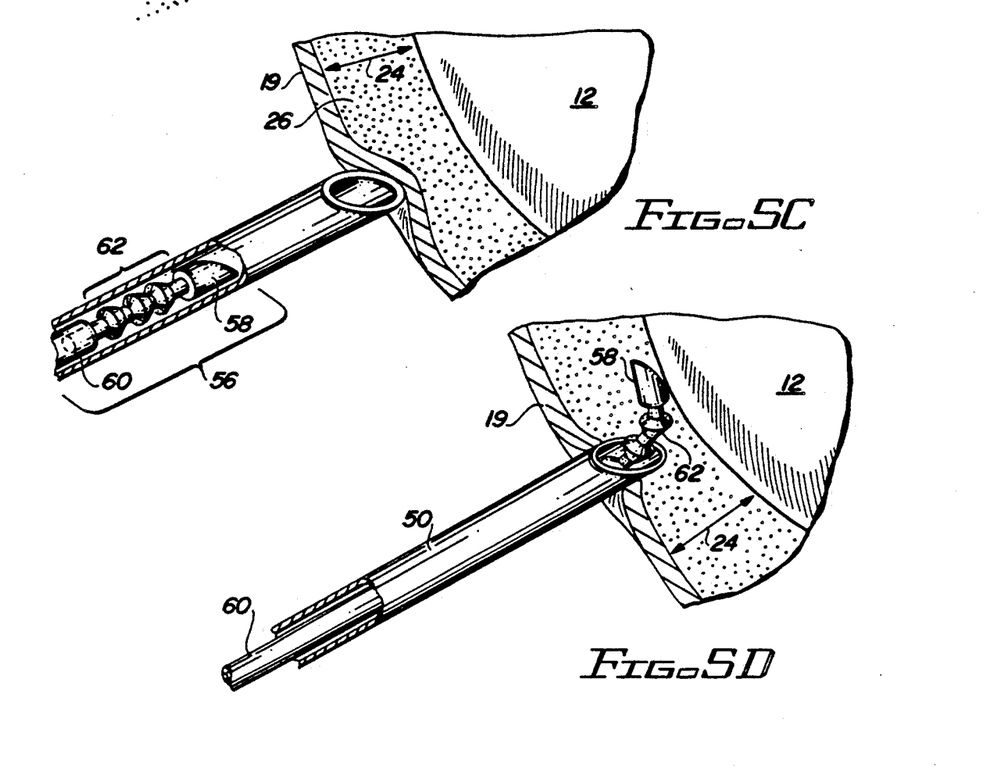
FIG. 5C is a view similar to FIG. 5A wherein a special perforation device is inserted in the lumen of the needle to aid in cutting through the pericardial wall.
FIG. 5D is a view as in FIG. 5C where the perforation device has punctured through the pericardial wall.

The coupling portion 62 joins the tip 58 to the body 60, and is designed to allow force applied to the handle or body portion 60 to be efficiently transferred to the tip portion 58. This cutting device 56 is inserted into the needle lumen and advanced, as required, applying a mild longitudinal force to the body portion 60 (to force the tip 58 against the pericardial wall 19), so as to have the tip 58 cleanly cut through the pericardial wall 19. Once the tip has cut through the wall 19, and without the lateral support of the needle lumen, the coupling portion 62 buckles, as shown in FIG. 5D.

The body portion 60 of the perforation device may be made from a conventional hollow wire or tube, or equivalent semi-rigid material, that can efficiently couple forces along its length. The tip portion 58 may be made from any suitable metal that can maintain a sharp edge, such as stainless steel. The coupling portion 62 may be a stainless steel compression spring or, more preferably, a molded bellows made from, for example, silicone rubber.

If the lumen of the needle or tube 50 is sufficiently large, it can function as the introducer through which other devices can be passed into the pericardial space 24, including the defibrillation lead 18. However, often a larger introducer is needed and/or a softer (polymeric) introducer is desired. In such instances, a method of enlarging the hole through the pericardial wall and introducing a sheath therein must be employed.

Figures 6A, 6B:
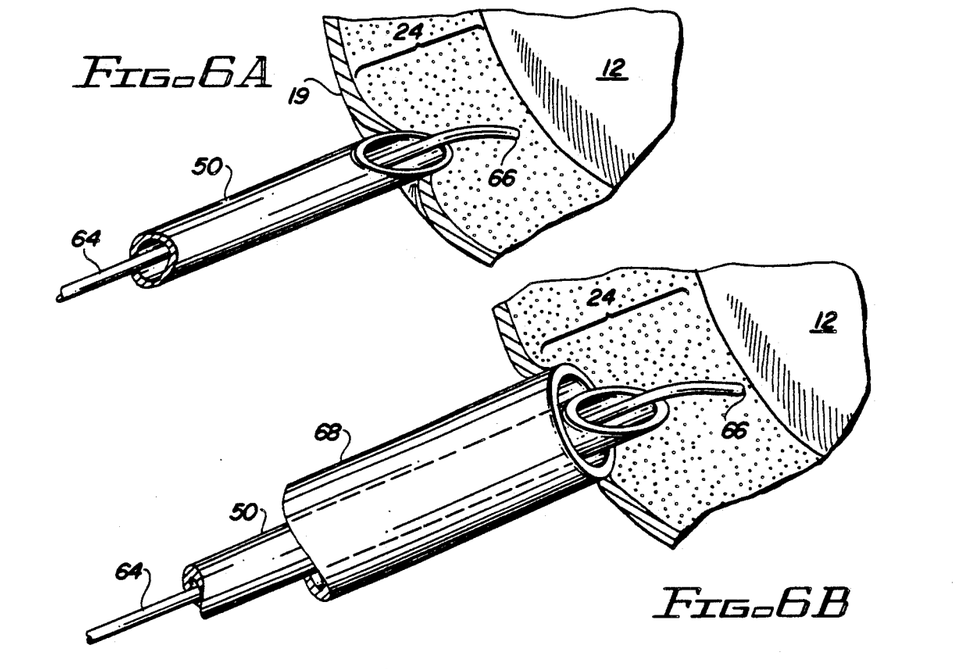
FIG. 6A is a view as in FIG. 5B further illustrating a guide wire or stylet inserted through the lumen of the needle into the pericardial space.
FIG. 6B is a view as in FIG. 6A further depicting a catheter inserted into the pericardial space over the needle and guide wire.

One such method is illustrated in FIGS. 6A and 6B. Referring first to FIG. 6A, a guide wire, having a blunt tip 66 is inserted through the lumen of the needle 50 so that the blunt tip is within the pericardial space 24. Then, depending upon the type and size of sheath to be inserted, the needle may be withdrawn and a suitable sheath 68 may be inserted over a dilator which slides over the guide wire 64. Alternatively, the sheath 68 may be inserted over both the needle 50 and guide wire 64, as shown in FIG. 6B, in which case the needle would not be withdrawn until after the distal end of the sheath has been inserted into the pericardial space 24. The guide wire may then be used to assist in introducing the defibrillation lead 18 into the pericardial space, as well as to assist in the positioning of the defibrillation electrode to a desired location within the pericardial space.

In general, conventional techniques may be used for inserting the sheath 68 into the pericardium 14. In a preferred introduction, the sheath 58 is simply inserted over the needle 50 and, through the application of a gentle longitudinal force on the sheath, the sheath is pushed through the hole, thereby dilating the hole in the pericardial wall so as to enlarge it sufficiently to allow introduction of the sheath. However, despite the fact that the pericardium is attached to the diaphragm, pushing against the pericardium (in order to force the sheath thereinto) may prove difficult without damaging the heart.

Accordingly, other possibilities for enlarging the pericardial hole may be considered. These possibilities include: (1) using an angioplasty style ballon across the hole; (2) inserting a deflated balloon into the pericardial space, inflating the ballon, and retracting the inflated balloon through the hole; (3) using a mechanical device that enlarges the hole by cutting it larger; (4) using a mechanical device that enlarges the hole by stretching it using a biopsy forceps technique, similar to a blunt dissection; (5) using a mechanical device that enlarges the hole by stretching it using an expanding mini collet; or (6) using a pleated sheath that can be inserted with its pleat(s) in a folded position, thereby providing a small diameter sheath, and then enlarged to provide a large diameter sheath, stretching the hole as it enlarges.

The blunt dissection approach mentioned above (item 3) contemplates the use of a narrow, blunt tapered pair (or multiplicity) of jaws, pivotally mounted for closing or expanding. These jaws are placed in the hole in their closed position, then spread apart to separate (or tear) the layers of tissue apart.

Figure 6C:
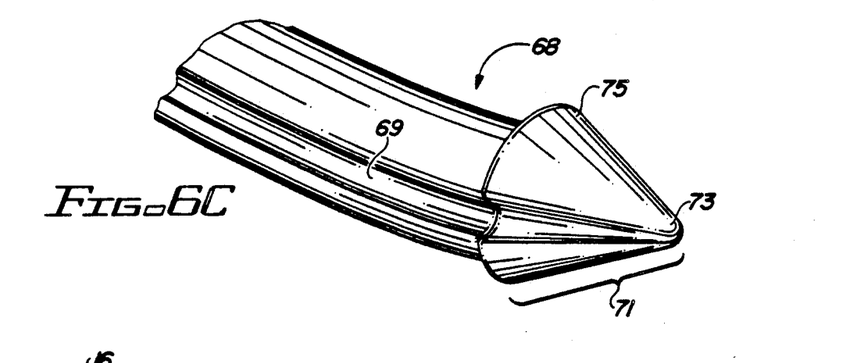
FIG. 6C is an elevated view of the distal tip of an expanding pleated sheath or catheter that may optionally be used to gain access into the pericardial space.

The pleated sheath approach mentioned above (item 6) contemplates the use of a sheath 68' having an expanding diameter. An elevated view of the distal end of such a sheath is illustrated in FIG. 6C. The sheath 68' includes at least one pleat 69 along the length thereof. This pleat simply comprises an integral section of the wall of the sheath that is folded into the interior of the sheath. Typically, the sheath 68' including its pleat 69 is made from a suitable biocompatible elastically expandable substance, such as silicone rubber.

A tip 71 at the distal end of the sheath 68' is tapered from a narrow tip portion 73 to a larger end portion 75. As seen in FIG. 6C, the tip 71 resembles a conical arrow head. (Note that the sheath 68' shown in FIG. 6C is shown partially expanded, intermediate its most narrow diameter position, wherein the pleat 69 is completely folded inside of the sheat body, and its widest diameter position, where the pleat 69 is not folded in to the interior of the sheath body at all.)

To enlarge the small hole in the pericardial wall, the sheath 68' is inserted over the guide wire and needle with the pleat(s) 69 completely folded into the sheath body, i.e., in its most narrow diameter position. The small portion of the tip 73 is inserted into the pericardial hole. The sheath is then expanded, using conventional means, as a gentle longitudinal force is exerted on the sheath in order to force the tip 71 deeper into the pericardial hole. As the sheath expands, and as the tip moves deeper into the hole, the hole is expanded by the increasingly wider tip 71. The sheath may then be fully expanded and inserted well into the pericardial space 24.

With the guide wire in place and the pericardial hole enlarged (and assuming a pleated sheath 68' is not already in place as above described), the sheath 68 is inserted well into the pericardial space 24 (FIG. 6B). Over the guide wire 64 and within the sheath 68, a suitable defibrillation electrode is advanced. It is noted that the preferred defibrillation electrode is deployable, having its electrode(s) in a retracted position while being inserted through the sheath.

However, it should be emphasized that this technique for sub-xiphoidally inserting a defibrillation lead would also have application to smaller, non-deployable defibrillation leads, of the type known in the art. Advantageously, a plurality of such leads and/or electrodes can be positioned in a desired configuration, such as an orthogonal configuration, within the pericardial space using this technique.

Figure 7:
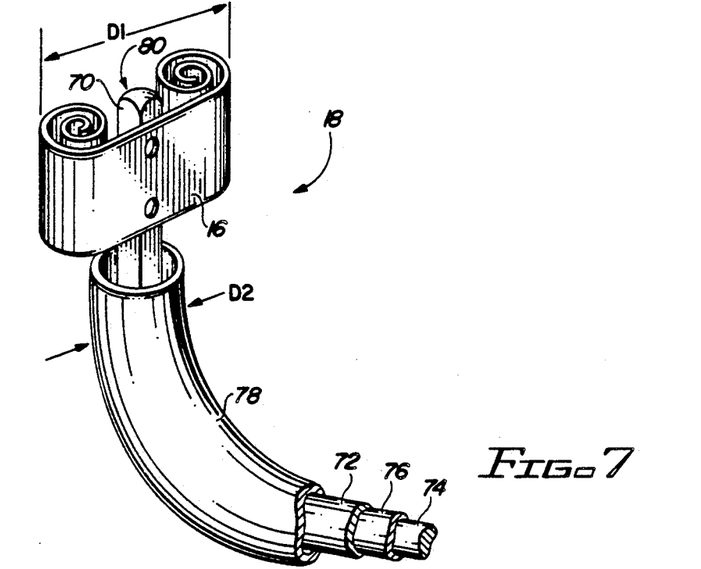
FIG. 7 shows the distal end of one type of defibrillation lead that could be used with the present invention, showing the electrode thereof in a partially retracted position.
Figure 8:
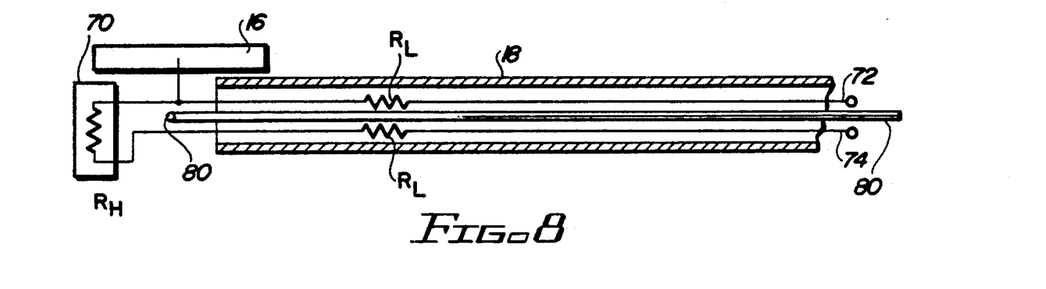
FIG. 8 is an electrical schematic diagram of the lead of FIG. 7.

Some possible deployable electrode configurations that lend themselves for use with the present invention are disclosed in the above-referenced patent application describing the transvenous implantation approach. Another possible electrode configuration is shown in FIGS. 7 and 8. FIG. 7 illustrates the distal end of the electrode 18 with its electrode 16, a butterfly type of patch electrode, partially coiled in its retracted position. When fully retracted, the electrode 16 is wound sufficiently tight so that the overall retracted dimension D1 is not much larger than the diameter of the body portion of the lead D2. This tight winding facilitates insertion of the lead/electrode into the sheath 68, which sheath 68 must have a diameter slightly larger than D1.

The distal tip of the electrode further includes a heating element 70, preferably protruding from the electrode somewhat so as to make good contact with the pericardium, the purpose and function of which is described below. The lead 18 typically includes two conductors 72 and 74, insulated from each other by an intermediate layer of insulating material 76. Typically, one conductor is spirally wound concentric with the other. An outer insulating sheath 78 insulates both conductors from body fluids.

A channel (or lumen) 80 through the center of the lead provides a space through which a guide wire may pass, and through which platelets or blood may be infused (as described below). This channel 80 exits at the distal tip near the heating element 70. The construction of two concentric conductor leads in this fashion is commonly practiced in the pacemaker lead art, where such two conductor leads are referred to as "bipolar" leads.

Alternatively, as will be evident from the description below, at least one of the two conductors, e.g., conductor 74, may be temporary, even removable. This is because this conductor only serves a purpose during the implant process. It is not needed after the implant has been completed. Hence, its inclusion in the lead 18 can be achieved inexpensively.

Two conductors 72 and 74 are employed in order to complete the circuit connection with the heating element 70, as shown in the electrical schematic diagram of the defibrillation lead in FIG. 8. If the heating element is not used, then a single lead conductor 72 could be used in unipolar fashion.

Figure 9:
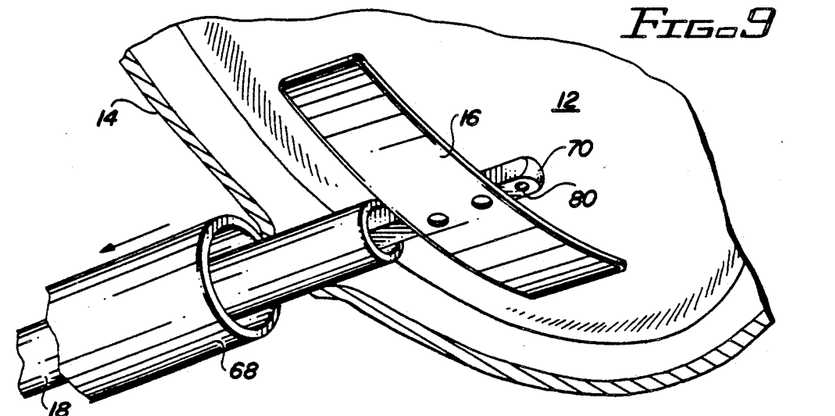
FIG. 9 is an exploded view of a section of the pericardial space and heart as in FIGS. 5A through 6B further illustrating the electrode of FIGS. 7 and 8 positioned within the pericardial space adjacent the heart.

Referring next to FIG. 9, with the electrode 16 in its fully retracted position, the lead 18 is inserted through the sheath 68 over the guide wire 66 (FIG. 6B). The guide wire is then used in conventional manner in order to position the electrode at a desired location within the cardiac space, and then the guide wire is withdrawn. The electrode 16 is deployed, as shown in FIG. 9, so as to make contact with the largest possible tissue area within the pericardium, and anchored in this position, as described below. The sheath 68 is then withdrawn, leaving just the electrode 18 entering the pericardial space.

Finally, as previously mentioned, and in conventional manner, the lead 18 is tunneled in the body tissue to a desired implant site where a suitable defibrillation device is implanted and connected to the lead 18. If desired, the defibrillation device need not be implanted, but need only be carried by the patient, and the lead 18 exits from the body tissue at a suitable site so as to be electrically connected thereto. Further details associated with techniques and methods for positioning and deploying the electrode 16 within the pericardial space may be found in the above-referenced transvenous implantation approach patent application.

One of the advantages of the present invention resides in the manner in which the electrode 16 is anchored to a desired location within the pericardial space. One such anchoring technique is to use conventional passive sclerosing pads or pericardioscope guided stapling or suturing. A better approach is to use an adhesive that is carried into the pericardial space on the non-deployed electrode. However, no biocompatible adhesives that may be applied to a beating heart are known to the applicant. However, the desired adhesion effect can advantageously be achieved by stimulating a fibrosis attachment site.

Such a site can be acutely accomplished by cautery (burning or searing). That is, just as a bleeding vessel can be coagulated by heat (RF, DC, laser or microwave cautery, for example), the present invention contemplates capturing or creating a clot on the patch electrode and coagulating it to the pericardium. As in coagulation of a bleeding vessel, external sources of heat, such as RF, DC, laser or microwave may be used to perform the cautery using conventional techniques. For example, a channel 80 may be provided down the spine of the electrode 16, or otherwise in contact therewith, through which wires for current (or optical fibers for laser) may pass. Further, infusion of platelets or whole blood may be passed through this channel 80.

The heater element 70, described above in connection with FIGS. 7 and 8, is a specific example of an electrical element that is used to coagulate (heat) platelets or whole blood that is passed through the channel 80 and over the heating element. The coagulated blood forms a bond with the pericardium. If needed, a small lesion may be created on the pericardium itself near the heater element to further promote adhesion.

The resistance of the heater element 70 should be carefully selected. On the one hand, this resistance should be kept as low as possible, to keep the applied voltage requirements within manageable limits, the power dissipated in the heating element being proportional to the square of the applied voltage V and inversely proportional to the resistance R. Hence, by keeping R small, a higher power dissipation is achieved for a given applied voltage.

On the other hand, the resistance needs to be kept as high as possible to avoid excessive Joule heating of the conductors. In other words, the resistance per unit length of the heating element needs to be large compared to the resistance per unit length of the conductors, yet not so large that enormous voltage levels must be applied thereto in order to achieve the desired heating of the element. These seemingly conflicting requirements are achieved by careful material selection and/or geometry. A suitable heating element material is Nichrome. The conductors 72 and 74 that make electrical contact with the heating element 70 may be standard biocompatible materials, such as MP35N wire.

It is further noted, as an alternative to passing whole blood or platelets through the channel 80 over the heater element 70, that an autologous blood clot may be formed in the lead near the electrode 16 before the implant. Once implanted, the heater element could be activated, in order to coagulate the blood clot to the pericardium. If this alternative is used, a pocket formed in the electrode tip near the heater element can hold the blood clot prior to implantation.

It is to be understood that the present invention also encompasses placement and anchoring of the electrode(s) to the epicardium or pleural sac, as such is also considered as being within the pericardium for purposes of the present invention.

Further, as has previously been mentioned, the techniques of placing and anchoring a defibrillation electrode as taught herein also find application when other approaches to access the heart, besides a sub-xiphoid approach, are utilized. For example, an intercostal access to the heart could be used.

It is also to be understood that the defibrillation electrode(s) could be positioned and/or anchored extra-pericardially, in accordance with the teachings of the present invention, using sub-xiphoid, intercoastal, or other access techniques.

EXAMPLES OF PERFORATION METHODS AND TECHNIQUES

The problem of perforating through one wall of tissue that is adjacent another wall of tissue raises the possibility that the puncturing mechanism or device may, unless it is controlled, puncture through both walls of tissue. Where sub-xiphoid or other access into the pericardial space is being attempted, a puncture through the pericardial wall is essential; but a puncture through the myocardial wall into the heart (either atrium or ventricle) is to be avoided. The best puncture method to use in a given situation depends largely upon the particular patient and his or her unique physiological makeup, the skill of the person performing the operation, and the availability of special equipment and tools.

The simplest, and perhaps the most effective, puncture technique is described above. Other possible puncture devices, techniques and methods are described below. Many of these devices and methods were originally conceived for the purpose of puncturing through the atrial lateral wall from within the heart (as accessed transvenously) without puncturing through the pericardial wall. However, these devices, methods and techniques are generally also applicable to puncturing through the pericardial wall from a sub-xiphoid or other percutaneous position without puncturing through the myocardial tissue of the heart.

A. CATHETER HAVING BUILT-IN PERFORATION MECHANISM

This technique was designed primarily for puncturing the atrial wall from the inside of the heart without puncturing the pericardial wall, and was designed to include a perforation mechanism inside of the guiding catheter, as operated by a guide wire in the catheter. (Guide wires are commonly used in transvenous placement of leads and catheters). However, the technique also has applicability to sub-xiphoid, intercostal or other puncturing of the pericardial wall if the device is made small enough to fit within the lumen of the needle or catheter through which access to the pericardium is obtained. In such case, the guide wire is used only to extend the perforating portion from a recessed position within the tip of the catheter or needle.

Figure 10A:
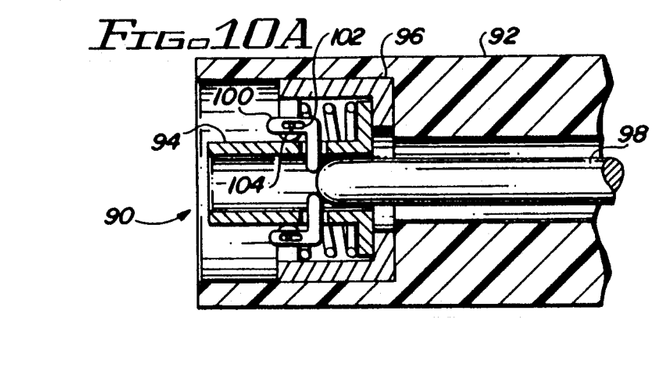
FIGS. 10A and 10B illustrate an alternate technique for piercing the pericardium without piercing the myocardium using an extendable piercing cylinder housed within the lumen of a special catheter.
Figure 10B:
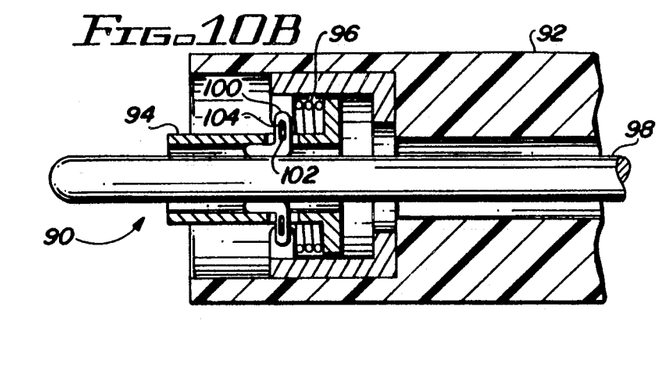

The device used for this technique is shown in FIGS. 10A and 10B, with FIG. 10A showing a perforation mechanism 90 in its retracted position, and FIG. 10B showing the perforation mechanism 90 in its extended position. The perforation mechanism 90 includes a catheter or other suitable housing 92 in which a perforation cylinder 94 is located. The perforation cylinder 94 is spring loaded, with a spring 96 or equivalent mechanism, within the tip of the housing 92 so that it is normally recessed therewithin. However, the cylinder 94 can be readily advanced by use of a simple guide wire 98.

As shown in FIGS. 10A and 10B, the cylinder 94 is coupled to the spring 96 by way of an arm 100 that includes a slot or detent 102 that engages a pivot pin 104. The guide wire 98 pushes the arms 100 so that they pivot and slide relative to the pivot pin 104, forcing the cylinder 94 out of its recessed position. Advantageously, the perforation cylinder 94 travels only a preset distance, yet the guide wire 98 can be advanced through the device as far as desired, as shown in FIG. 10B. Because the guide wire, once extended, is unsupported by the catheter, it easily buckles, making it extremely unlikely that the myocardial tissue will be perforated.

Note in FIG. 10A that the perforation cylinder 94 may be shaped to reduce the perforation force. As the guide wire is advanced several millimeters beyond that shown in FIG. 10A, the perforation cylinder 94 is forced out of the catheter 92, perforates the pericardial wall, whereupon the guide wire 98 can be advanced, if desired, into the pericardial space. The perforation cylinder 94 is shown in its extended position in FIG. 10B.

Of course, many variations of the perforation catheter 90 shown in FIGS. 10A and 10B could be envisioned by those skilled in the art. The important features of such a device are: (1) the perforation tool 94 is recessed within the catheter 92 until it is ready to be used; (2) the perforation tool (perforation cylinder) can not advance past the tip more than a precisely controlled distance; (3) the guide wire 98 is compelled to enter the hole once created so that the entry site to the pericardium can not be "lost"; and (4) the guide wire tip is soft (not able to support appreciable compressive loads along its axis without buckling) so it will not go through the pericardial space and perforate the myocardial tissue.

B. SUCTION DEVICES

In order to better control the entry into the pericardium, another technique is to contain the perforating instrument and pull the pericardial wall toward it. One technique for doing this is through the use of suction. One embodiment, shown in FIGS. 11A and 11B, includes a catheter 110, having a large soft tip 112, the catheter being guided to the desired perforation site over the sub-xiphoid (or other percutaneously inserted) needle. Once the catheter is in place, the needle can be removed, if desired.

Figure 11A:
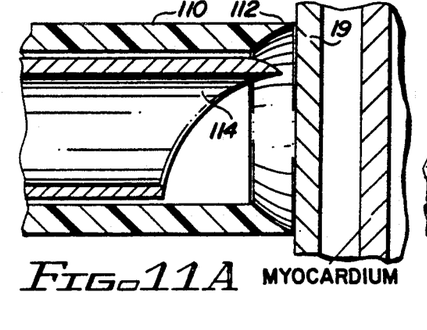
FIGS. 11A and 11B illustrate still another technique for using suction.

The tip 112 is fitted as tightly as possible up against the pericardial wall 19 in order to maintain and seal the suction force. Recessed within the tip 112 is an exquisitely sharp instrument 114. As suction is applied, the pericardial wall 19 is pulled into the catheter tip 112 and is impaled on the cutting instrument 114, and the perforation is made. Once made, a guide wire can be readily inserted into the pericardial space. With no suction applied, the catheter is as shown in FIG. 11A. With suction applied, it is as shown in FIG. 11B.

Figure 11B:
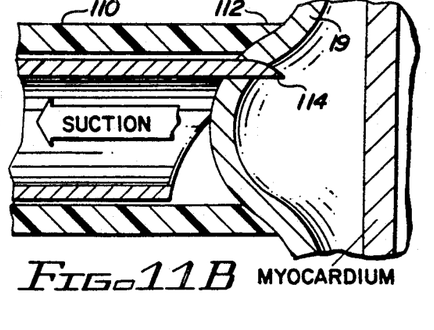

As can be seen from FIG. 11B, with suction applied the heart tissue is not in danger of being pierced by the piercing tip 114. Further, although not shown, it should be noted that a suitable hemostasis valve can be used, as required, so that suction can be applied with the guide wire and perhaps even the sub-xiphoid needle in position.

C. SUCTION DEVICES WITH MECHANICAL BACKUP

One of the potential problems with using a suction device as described above is that suction may be lost. To lessen the risk of such event, at least one form of mechanical active fixation could be used with the suction. Such active fixation may take the form of a helical screw. Alternatively, a remotely operated wire suture could be used, as shown below in FIGS. 12A-12B. The use of more than one suture or ribbon wire would increase stability.

Figure 12A:
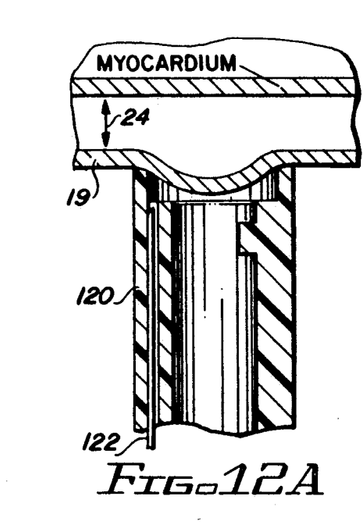
FIGS. 12A–12D illustrate yet another technique for piercing the pericardium using a pre-formed suture.
Figure 12B:
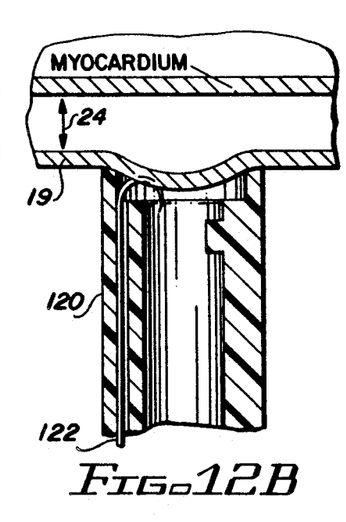
Figure 12C:
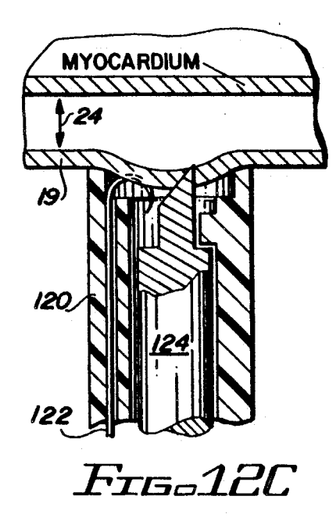
Figure 12D:
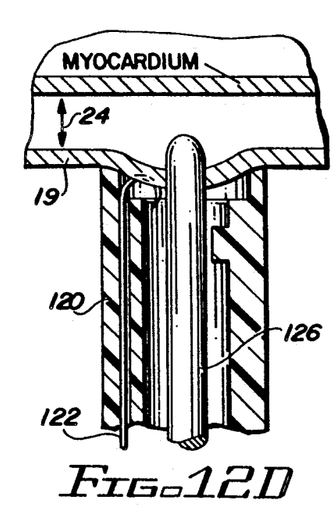

As seen in FIG. 12A, a catheter 120 without piercing implement is placed against the pericardial wall 19. Suction is drawn, thus pulling the pericardial wall 19 into the lumen of the catheter 120. With the pericardial wall safely separated from the myocardial tissue, the suture(s) is placed. This is done by advancing a preformed tight radius wire 122 out of the catheter 120. The wire 122 pierces a "bite" of the pericardial wall, thus stabilizing the catheter tip. Once stabilized, the piercing can be safely performed within the recess of the catheter by inserting a piercing needle 124 through the lumen of the catheter 120 until the desired piercing has been completed. Once pierced, a suitable guide wire 126 can be inserted into the pericardial space. This complete sequence is illustrated in FIGS. 12A-12D.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as within the scope of the present invention.

What is claimed is:

1. A method of percutaneously implanting a defibrillation lead within the intrapericardial space of a patient's heart, the defibrillation lead having a distal electrode, a body, and proximal connection means capable of making electrical contact to an implantable defibrillation device, the method comprising the steps of:
   distending the pericardium from the epicardium by injecting a small volume of fluid into the pericardium, so that pericardial effusion results;
   percutaneously perforating the pericardium by advancing a perforation device having a lumen therethrough towards the distended pericardium until the fluid flows out of the lumen, thereby indicating that the pericardium wall has been perforated;
   inserting a guide wire into the pericardium through the lumen of the perforation device until a distal end thereof is positioned within the pericardium;
   enlarging the perforated opening in the pericardium by inserting an introducer over the guide wire and into the tissue; and
   inserting the distal electrode of the defibrillation lead within the introducer until the distal electrode is likewise positioned within the pericardium.

2. The method of claim 1 wherein the step of distending the pericardium comprises:
   transvenously attaching a screw-in catheter to the right atrial lateral wall;
   advancing a stylet having a tip through the catheter until the tip contacts the atrial wall;

puncturing the atrial wall with the tip of the stylet; and infusing the small volume of fluid through the catheter into the pericardium.

3. The method of claim 1 wherein the step of perforating the pericardium comprises:

plugging the lumen of the perforation device with a relatively rigid rod prior to inserting the perforation device, the rigid rod preventing tissue coring as the perforation device is inserted;

inserting the perforation device and rod only until a tip of the perforation device is abutted against the pericardium;

removing the rigid rod from the lumen; and perforating the pericardium at the point where the perforation device tip is abutted against the pericardium, thereby making an opening in the pericardium through which the perforation device tip may be inserted.

4. The method of claim 3 wherein the step of perforating the pericardium at the point where the perforation device is abutted against the pericardium further comprises inserting a cutting device into the lumen and cutting an opening through the pericardium wall using the cutting device.

5. The method of claim 1 wherein the step of inserting the guide wire into the distended pericardium comprises inserting the guide wire into the distended pericardium from a sub-xiphoid position.

6. The method of claim 1 wherein the step of inserting the guide wire into the distended pericardium comprises inserting the guide wire into the distended pericardium from an intercostal position.

7. The method of claim 1 further comprising the step of tunneling the body of the defibrillation lead to a desired tissue location, whereat the proximal connection means of the defibrillation lead may be connected to a desired defibrillation device.

8. The method of claim 1 wherein the step of inserting the distal electrode into the pericardium further comprises the step of anchoring the distal electrode within the pericardium.

9. The method of claim 8 wherein the step of anchoring the distal electrode within the pericardium comprises the step of stimulating a fibrosis attachment site within the pericardium whereat the distal electrode may be anchored.

10. The method of claim 9 wherein the defibrillation lead further comprises a heating element at its distal tip, and wherein the step of anchoring the distal electrode within the pericardium further comprises acutely attaching the distal electrode to the heart by selectively energizing the heating element.

11. The method of claim 8 wherein the step of anchoring the distal electrode within the pericardium comprises the step of capturing an autologous blood clot on the distal electrode and coagulating it to the pericardium.

12. The method of claim 11 further comprising the step of creating a small lesion on the pericardium to promote adhesion of the coagulated blood clot thereto.

13. The method of claim 12 wherein the steps of coagulating the blood clot and creating a small lesion of the pericardium further comprise selectively applying energy from an external source to the site of attachment.

14. The method of claim 13 wherein the step of applying external energy to the site of attachment comprises directing microwave energy from an external microwave source on the site of attachment.

15. The method of claim 13 wherein the step of applying external energy to the site of attachment comprises directing laser energy form an external laser source to the site of attachment.

16. The method of claim 13 wherein the defibrillation lead further comprises a heating element at its distal tip at the site of attachment and electrical means for directing electrical energy to the heating element, and wherein the step of applying external energy to the site of attachment comprises applying electrical energy to the heating element through said electrical means.

17. The method of claim 1 wherein the defibrillation lead comprises a deployable defibrillation lead having a retracted position wherein the distal electrode thereof is maintained in a retracted position, and a deployed position wherein the distal electrode is extended so as to provide a larger electrode surface area, and further wherein the step of inserting the distal electrode of the defibrillation lead comprises inserting the distal electrode through the introducer while in its retracted position and extending the distal electrode to its deployed position after the distal electrode has been inserted within the pericardium.

18. A method of positioning at least one defibrillation lead within the pericardium of a mammal, the defibrillation lead having deployable distal electrode means for selectively placing an electrode in contact with a desired tissue area when the electrode is deployed, and for selectively maintaining the electrode in a retracted position, thereby facilitating the movement and positioning of the electrode until the electrode is positioned at a desired tissue location, the method comprising the steps of:

(a) injecting a fluid between the heart and the pericardium, thereby extending the pericardium away from the heart;

(b) percutaneously inserting a guide wire having a lumen therethrough into the extended pericardium at a desired tissue contact location until the fluid injected between the heart and the pericardium flows out of the lumen, thereby indicating that the pericardium wall has been perforated;

(c) placing a sheath introducer into the pericardium over the guide wire;

(d) inserting the electrode, in its retracted position, within the pericardium through the sheath introducer; and (e) deploying the electrode within the pericardium, whereby the electrode makes contact with a large tissue area at the desired tissue contact location within the pericardium.

19. The method of claim 18 wherein the step of injecting a fluid between the heart and the pericardium comprises:

transvenously attaching a screw-in catheter to the right atrial lateral wall of the heart;

advancing a stylet through the catheter until a tip of the stylet contacts the atrial wall;

puncturing a small hole in the atrial wall with the tip of the stylet; and injecting the fluid through the catheter and through the punctured hole in the atrial wall into the space between the heart and the pericardium.

20. The method of claim 18 wherein the step of percutaneously inserting the guide wire comprises inserting the guide wire into the distended pericardium from a sub-xiphoid position.

21. The method of claim 18 wherein the step of deploying the electrode further comprises recording the ECG of said mammal to aid in correctly positioning the electrode.

22. A method for anchoring a distal electrode of a defibrillation lead within the pericardium comprising the steps of:
 (a) capturing an autologous blood clot on the distal electrode;
 (b) inserting the distal electrode within the pericardium; and
 (c) coagulating the blood clot to tissue within the pericardium.

23. The method of claim 22 wherein step (c) further comprises creating a small lesion in the tissue at the desired attachment site within the pericardium to promote adhesion of the coagulated blood clot thereto.

24. The method of claim 23 wherein step (c) further comprises applying external energy to the desired attachment site to create said lesion.

25. The method of claim 24 wherein said defibrillation lead further comprises electrical means for directing electrical energy to the distal electrode thereof, and wherein the step of applying external energy to the site of attachment comprises applying electrical energy to the site of attachment through said electrical means.

26. The method of claim 24 wherein the step of applying external energy to the site of attachment comprises guiding microwave energy from an external source to the site of attachment.

27. The method of claim 24 wherein the step of applying external energy to the site of attachment comprises selectively guiding electromagnetic energy from an external source to the site of attachment.

28. A system for implanting a defibrillation lead in a mammal, the mammal having a heart surrounded by a pericardium, the system comprising:
 a defibrillation lead having a deployable distal electrode that selectively assumes a retracted position adapted to promote the positioning of the distal electrode without having the distal electrode becoming entangled with body tissue, and an extended position adapted to promote contact with body tissue over a large area, the defibrillation lead having deployment means for extending the distal electrode to its extended position;
 means for injecting a fluid between the heart and the pericardium, thereby extending the pericardium away from the heart;
 a perforation device having a lumen therethrough, the perforation device being sub-xiphoidally inserted toward the extended pericardium until the fluid flows out of the lumen, thereby indicating that the extended pericardium wall has been perforated; and
 insertion means for inserting the defibrillation lead, with its deployable distal electrode in its retracted position, into the pericardium until the distal electrode is positioned at a desired location within the pericardium.

29. The system of claim 28 wherein the defibrillation lead comprises anchoring means for anchoring the distal electrode to the body tissue.

30. The system of claim 29 wherein said anchoring means comprises means for capturing a blood clot on the distal electrode and means for coagulating said blood clot to desired tissue within the pericardium.

31. The system of claim 30 further comprising means for making a small lesion within the pericardium, said blood clot adhering to said small lesion as coagulation occurs.

32. The system of claim 29 wherein said anchoring means comprises a heater element within the distal electrode and means for applying electrical energy thereto, and wherein heat generated by said heater element creates a fibrosis attachment site within the pericardium whereat the distal electrode is anchored.

33. The system of claim 28 wherein the perforation device comprises:
 a blunt needle having a removable, rigid rod therethrough, the rod being capable of preventing tissue coring as the needle is advance into the pericardium.

34. The system of claim 28 wherein the perforation device comprises:
 a housing; and
 a cutting device within the housing, the cutting device having a sharp cutting tip, a rigid body portion and a flexible, compressible coupling portion located between the body portion and the tip, the coupling portion being capable of transferring longitudinal forces from the body portion to the tip while in the housing, and further being capable of buckling without the lateral support of the housing.

35. The system of claim 28 wherein the perforation device comprises:
 a percutaneous insertion needle;
 a catheter having a blunt soft tip, the catheter being guided to the pericardium over the insertion needle;
 a cutting device recessed with the catheter;
 means for applying suction between the catheter tip and the pericardium so that the pericardium is pulled into the catheter tip and impaled on the cutting device, thereby perforating the pericardium.

36. The system of claim 35 wherein the perforation device further comprises:
 a remotely activated fixation device located within the catheter for fixating the catheter tip against the pericardium when the fixation device is activated.

37. A defibrillation lead system comprising:
 a sheath;
 means for passing said sheath through a pericardium surrounding a heart from a percutaneous position;
 a defibrillation lead having a distal electrode, said defibrillation lead being of a size that allows it to be slidably inserted through said sheath until said distal electrode resides within the pericardium; and
 means for anchoring said distal electrode to a desired location within the pericardium, said anchoring means comprising means for stimulating a fibrosis attachment site.

38. The lead system of claim 37 wherein said anchoring means comprises means for capturing a blood clot on said distal electrode and means for coagulating said blood clot to a desired attachment site within the pericardium.

39. The lead system of claim 38 wherein said anchoring means further comprises means for creating a small lesion in the body tissue at the desired attachment site, which small lesion promotes the adhesion of the coagulated blood clot thereto.

40. The lead system of claim 37 wherein said anchoring means comprises means for passing platelets or whole blood near said distal electrode and means for coagulating said platelets or whole blood to a desired attachment site within the pericardium.

41. The lead system of claim 40 wherein said anchoring means further comprises means for creating a small lesion in the body tissue at the desired attachment site, which small lesion promotes the adhesion of the coagulated blood clot thereto.

* * * * *